(12) United States Patent
Han et al.

(10) Patent No.: US 11,273,447 B2
(45) Date of Patent: Mar. 15, 2022

(54) COLLAPSIBLE BASKET ARRAYS, COLLAPSIBLE CELLULAR ARRAYS THEREFOR, AND METHODS OF USE

(71) Applicant: Purdue Research Foundation, West Lafayette, IN (US)

(72) Inventors: Bumsoo Han, West Lafayette, IN (US); George Tsu-Chih Chiu, West Lafayette, IN (US); Thomas Heinrich Siegmund, West Lafayette, IN (US); Michael Linnes, West Lafayette, IN (US); Yumeng Wu, West Lafayette, IN (US); Matthew Tyler Short, Sudbury, MA (US)

(73) Assignee: Purdue Research Foundation, West Lafayette, IN (US)

( * ) Notice: Subject to any disclaimer, the term of this patent is extended or adjusted under 35 U.S.C. 154(b) by 181 days.

(21) Appl. No.: 16/741,222

(22) Filed: Jan. 13, 2020

(65) Prior Publication Data
US 2020/0222898 A1 Jul. 16, 2020

Related U.S. Application Data

(60) Provisional application No. 62/791,169, filed on Jan. 11, 2019.

(51) Int. Cl.
*C12M 3/00* (2006.01)
*C12M 1/00* (2006.01)
*B01L 3/00* (2006.01)

(52) U.S. Cl.
CPC ........... *B01L 3/5055* (2013.01); *C12M 23/26* (2013.01); *C12M 23/42* (2013.01);
(Continued)

(58) Field of Classification Search
CPC . C12M 23/26; C12M 23/42; B01L 2200/021; B01L 2200/022
See application file for complete search history.

(56) References Cited

U.S. PATENT DOCUMENTS

| | | | | |
|---|---|---|---|---|
| 6,277,630 B1* | 8/2001 | Brophy | ................ | B01L 3/5085 422/503 |
| 7,598,076 B2* | 10/2009 | Wedell | .................... | B01L 3/508 435/297.5 |

(Continued)

OTHER PUBLICATIONS

Kang, J. et al., "Mini-Pillar Array for Hydrogel-Supported 3D Culture and High-Content Histologic Analysis of Human Tumor Spheroids", Lab Chip, (2016), 16, pp. 2265-2276.

(Continued)

*Primary Examiner* — Nathan A Bowers
(74) *Attorney, Agent, or Firm* — Hartman Global IP Law; Gary M. Hartman; Domenica N. S. Hartman

(57) ABSTRACT

Multi-well collapsible basket arrays and methods for their use with high throughput culture and histology analysis of spheroids and organoids. Such a collapsible basket array includes a collapsible cellular array structure having multiple cells and connectors that interconnect adjacent pairs of the cells to cause the collapsible cellular array structure to collapse from an expanded configuration to a collapsed configuration in which the connectors are partially wrapped around perimeters or circumferences of the cells, whereby the collapsible cellular array structure is expandable to acquire an expanded configuration capable of individually aligning the cells thereof with wells of a well plate. The collapsible basket array further includes inserts individually mountable to the cells of the collapsible cellular array structure, with each insert including a permeable basket with pores sized to retain spheroids or organoids within the basket.

20 Claims, 7 Drawing Sheets

(52) U.S. Cl.
CPC . *B01L 2200/021* (2013.01); *B01L 2300/0893* (2013.01); *B01L 2300/123* (2013.01)

(56) References Cited

U.S. PATENT DOCUMENTS

| | | | | |
|---|---|---|---|---|
| 2008/0261306 | A1* | 10/2008 | Neumann | C12M 23/20 |
| | | | | 435/395 |
| 2011/0240194 | A1* | 10/2011 | Summers | B32B 3/12 |
| | | | | 152/246 |
| 2014/0027333 | A1* | 1/2014 | Pawlowski | A61M 5/001 |
| | | | | 206/438 |
| 2020/0156840 | A1* | 5/2020 | Komann | B65D 1/36 |
| 2020/0309705 | A1* | 10/2020 | DeJong | B01L 9/06 |
| 2021/0162408 | A1* | 6/2021 | Sabaawy | B01L 3/50855 |

OTHER PUBLICATIONS

Lee, D.W. et al., "Pitch-Tunable Pillar Arrays for High-Throughput Culture and Immunohistological Analysis of Tumor Spheroids", RSC Adv., (2018) 8, pp. 4494-4502.

Prall et al., "Properties of a Chiral Honeycomb with a Poisson's Ratio of -1", Int. J. Mech. Sci. vol. 39, No. 3, (1997) pp. 305-314.

\* cited by examiner

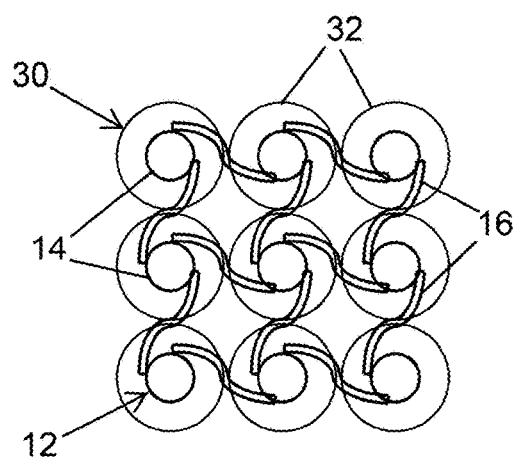
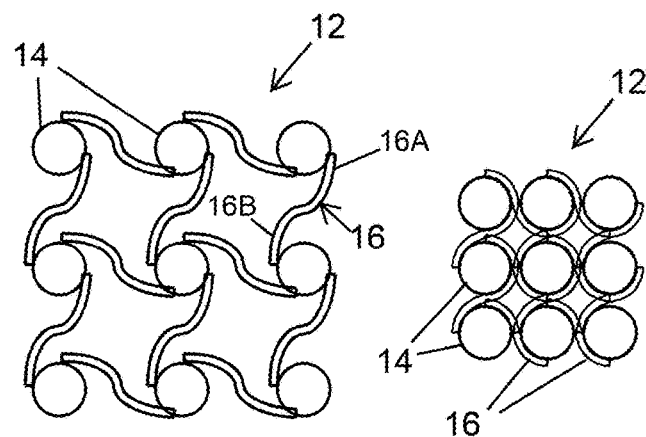
FIG. 6  FIG. 5  FIG. 4
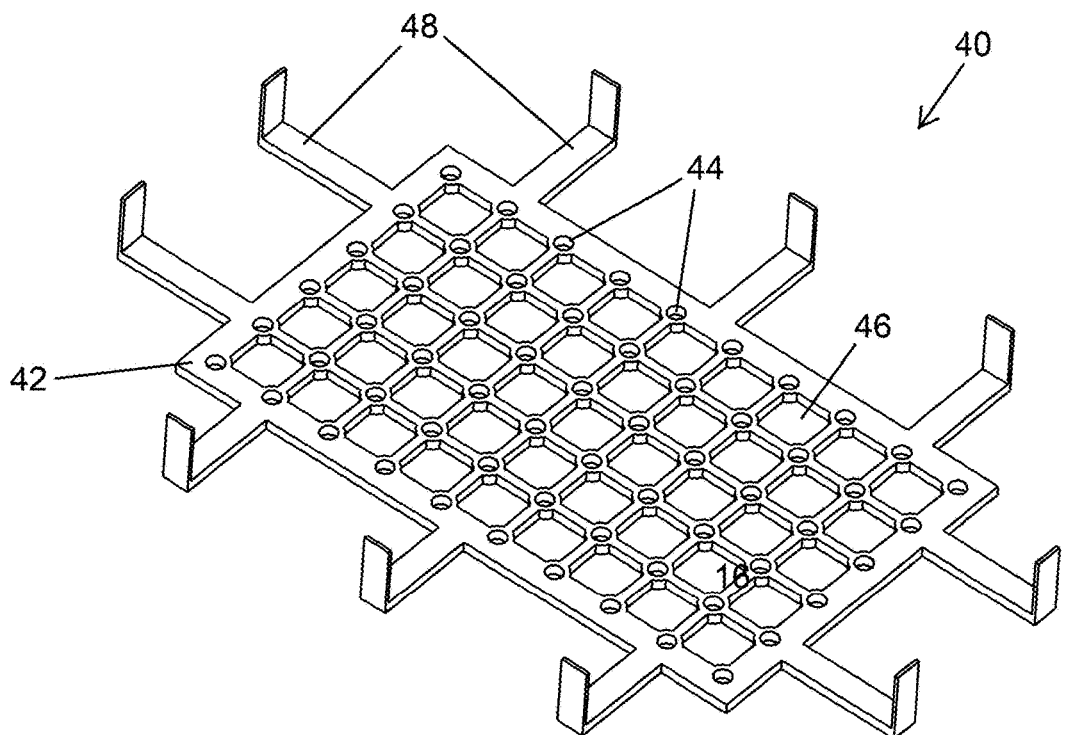
FIG. 7

COLLAPSIBLE BASKET ARRAYS, COLLAPSIBLE CELLULAR ARRAYS THEREFOR, AND METHODS OF USE

CROSS-REFERENCE TO RELATED APPLICATIONS

This application claims the benefit of U.S. Provisional Application No. 62/791,169, filed Jan. 11, 2019, the contents of which are incorporated herein by reference.

STATEMENT OF GOVERNMENT SUPPORT

This invention was made with government support under the agreement 18x091, which is part of Contract HHSN261200800001E, issued by the National Cancer Institute, National Institute of Health. The government has certain rights in the invention.

FIELD OF INVENTION

This disclosure relates to multi-well collapsible basket arrays suitable for use with high throughput culture and histology analysis of tumor spheroids and organoids.

BACKGROUND

Incorporating 3D cell cultures with high throughput screening (HTS) processes is still in its infancy, but shows promise in directly identifying clinically relevant compounds and enabling effective translational research. Unfortunately, not all 3D cell culture models are compatible with HTS in a routine and cost-effective manner. For example, cultured spheroids or organoids in rigid wells need to be manually transferred by single-channel pipetting to separate containers (for example, cassettes) for subsequent histology analysis. This process tends to disrupt the culture's original features. Therefore, there is a need to directly act on the original culture array for various analysis for diagnosis, drug discovery, etc.

SUMMARY OF THE INVENTION

This disclosure provides multi-well collapsible basket arrays, systems that incorporate the arrays, and the use of the arrays for high throughput culture and histology analysis of spheroids and organoids.

According to one aspect of the invention, a collapsible basket array includes a collapsible cellular array structure comprising multiple cells and connectors that interconnect adjacent pairs of the cells to cause the collapsible cellular array structure to collapse from an expanded configuration to a collapsed configuration in which the connectors are partially wrapped around perimeters of the cells, whereby the collapsible cellular array structure is expandable to acquire an expanded configuration capable of individually aligning the cells thereof with wells of a well plate. The collapsible basket array further includes a plurality of inserts individually mountable to the cells of the collapsible cellular array structure, the permeable baskets having pores sized to retain spheroids or organoids within the baskets.

According to another aspect of the invention, a system is provided for directly transferring cultured spheroid or organoid into a histology cassette or other high throughput analysis configuration. The system includes a collapsible basket array of a type described above, a spacer grid configured to maintain the collapsible cellular array structure in the expanded configuration thereof, and a separator plate configured to release the collapsible cellular array structure from the spacer grid to enable the collapsible basket array to collapse toward the collapsed configuration.

According to yet another aspect of the invention, a method is provided for performing culture and histology analysis of spheroids or organoids. The method includes the use of a collapsible basket array that comprises a collapsible cellular array structure and a plurality of inserts. The collapsible cellular array structure comprises multiple cells and connectors that interconnect adjacent pairs of the cells to cause the collapsible cellular array structure to collapse from an expanded configuration to a collapsed configuration, whereby the collapsible cellular array structure is expandable to acquire the expanded configuration. The inserts are individually mounted to the cells of the collapsible cellular array structure, and each insert comprises a permeable or semipermeable basket having pores sized to retain spheroids or organoids within the baskets. The method further includes expanding the collapsible cellular array structure to acquire the expanded configuration capable thereof, individually aligning the inserts of the collapsible basket array with wells of a well plate, inserting the inserts individually into the wells of the well plate, culturing spheroids or organoids in the baskets of the inserts, displacing the collapsible basket array from the well plate to remove the inserts from the wells of the well plate, collapsing the collapsible basket array to the collapsed configuration thereof, and placing the collapsible basket array in a cassette.

Various features, aspects and advantages of the present invention will become better understood with reference to the following drawings, associated descriptions, and claims.

BRIEF DESCRIPTION OF THE DRAWINGS

FIG. 4 schematically represents a collapsible cellular array structure of the type represented in FIGS. 1 and 3, wherein the array structure is in a collapsed configuration that the array structure assumes in the absence of a force (or forces) capable of expanding the array structure, so that the array structure can be placed within a histology cassette.

FIG. 5 schematically represents the collapsible cellular array structure of FIG. 4 in an expanded configuration, for example, similar to those depicted in FIGS. 1 and 3, which the cellular array structure assumes in the presence of a biaxial force capable of expanding the cellular array structure.

FIG. 6 schematically represents the collapsible cellular array structure of FIGS. 4 and 5 in the expanded configuration with individual cells thereof individually aligned with wells of a multi-well plate.

FIG. 7 schematically represents a spacer grid adapted to apply biaxial forces capable of expanding and maintaining a collapsible cellular array structure in its expanded configuration.

DETAILED DESCRIPTION OF THE INVENTION

Figure 1:
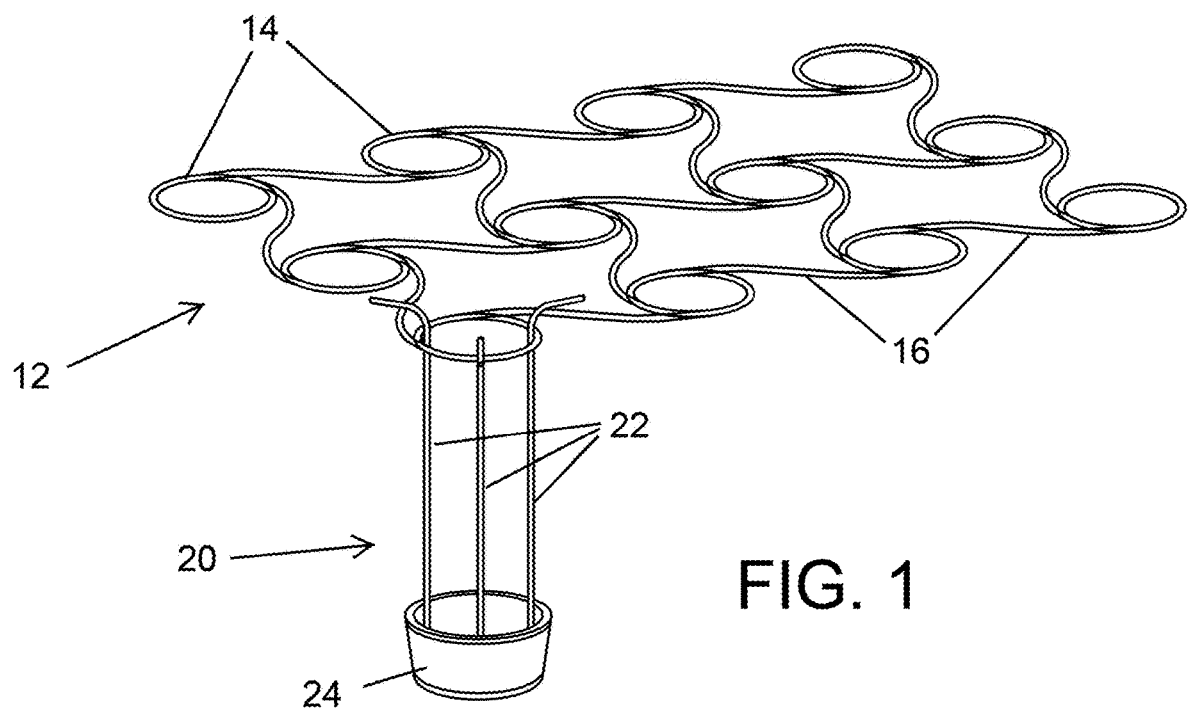
FIG. 1 schematically represents a nonlimiting embodiment of an expanded but collapsible cellular array structure and a permeable insert placed in one of a plurality of cells of the cellular array structure to form a collapsible basket array suitable for use with multi-well plates of types used for culture and histology analysis of spheroids and organoids.

While certain aspects of the present disclosure are illustrated in the drawings and described below, the drawings and description are to be considered as exemplary and not restrictive in character; it being understood that only the illustrative embodiments are shown and described and that all changes and modifications that come within the spirit of the disclosure are desired to be protected.

For convenience, consistent reference numbers are used throughout the drawings to identify the same or functionally related/equivalent elements. Unless defined otherwise, the scientific and technology nomenclatures have the same meaning as commonly understood by a person in the ordinary skill in the art pertaining to this disclosure.

FIG. 1 schematically represents a nonlimiting embodiment of a collapsible basket array 10 suitable for use with multi-well plates during culture and histology analysis of spheroids or organoids. As a nonlimiting example, the collapsible basket array 10 may be designed to transfer spheroids or organoids cultured in a standard multi-well plate into a deep histology cassette of types commonly used in microscopy, while maintaining its original array registry so that the cultured spheroids and organoids can be processed, paraffin-embedded and sectioned as a microarray.

The collapsible basket array 10 is shown as comprising a collapsible cellular array structure 12 containing an array of cells 14, each individually sized for mounting or attaching an insert 20 thereto. The inserts 20 can be of any suitable type that has a basket 24 or other suitable means capable of containing and retaining spheroids or organoids, whose sizes typically range from about twenty to a few hundred micrometers, during culture and histology processing. The cellular array structure 12 of FIG. 1 is represented as a 3×4 array, though it should be understood that the cellular array structure 12 is not limited to any particular size of array. However, an 8×12 cellular array structure 12 would ordinarily be a preferred embodiment for use with 96-well plates commonly used in the art.

Figure 2:
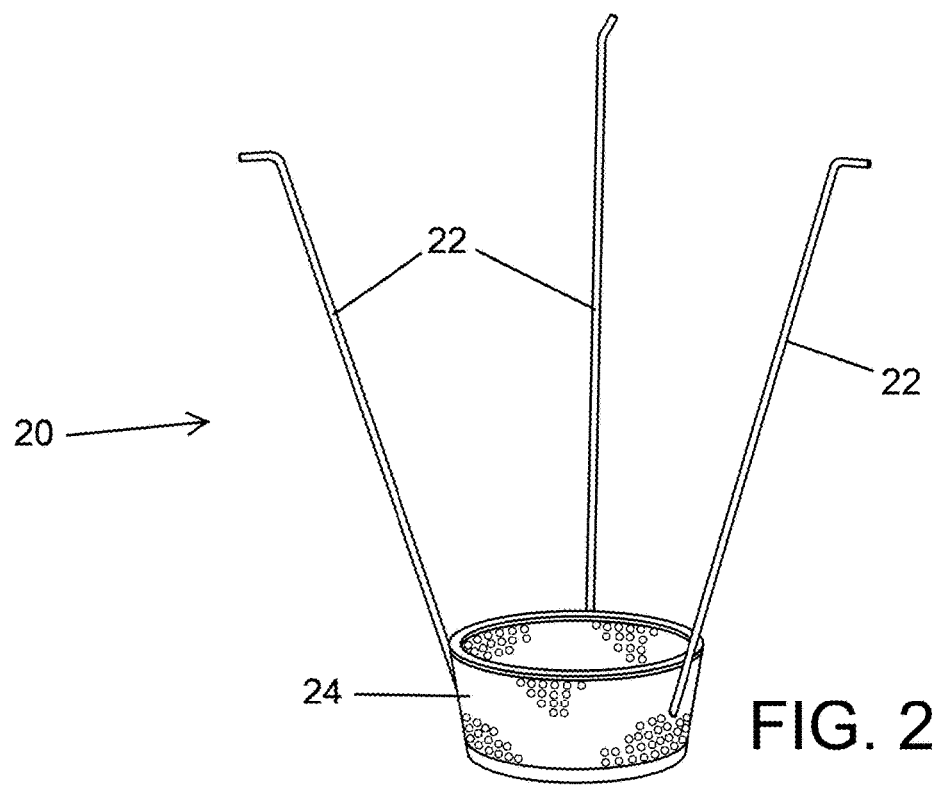
FIG. 2 schematically represents an isolated view of the permeable strainer insert of FIG. 1, wherein the insert is adapted to hold spheroids or organoids during culture and histology processing.

The cells 14 are relatively rigid, or at least more rigid than connectors 16 that interconnect adjacent pairs of cells 14 and are preferably capable of being elastically deformed. In FIG. 1, the cells 14 and connectors 16 have round wire-like cross-sections, though other cross-sectional shapes are foreseeable. The cells 14 of the cellular array structure 12 are represented as generally circular-shaped to form ring or annulus that defines and surrounds a central opening. As evident from FIG. 1, each cell 14 is adapted to support a single insert 20, of which only one is represented in FIG. 1. In the nonlimiting embodiment of FIG. 1, the insert 20 has multiple arms 22 by which its basket 24 can be coupled to and supported from a cell 14 of the cellular array structure 12. As evident from FIGS. 1 and 2, the basket 24 is in the form of a permeable or semipermeable mesh cup, though other configurations are foreseeable.

Figure 3:
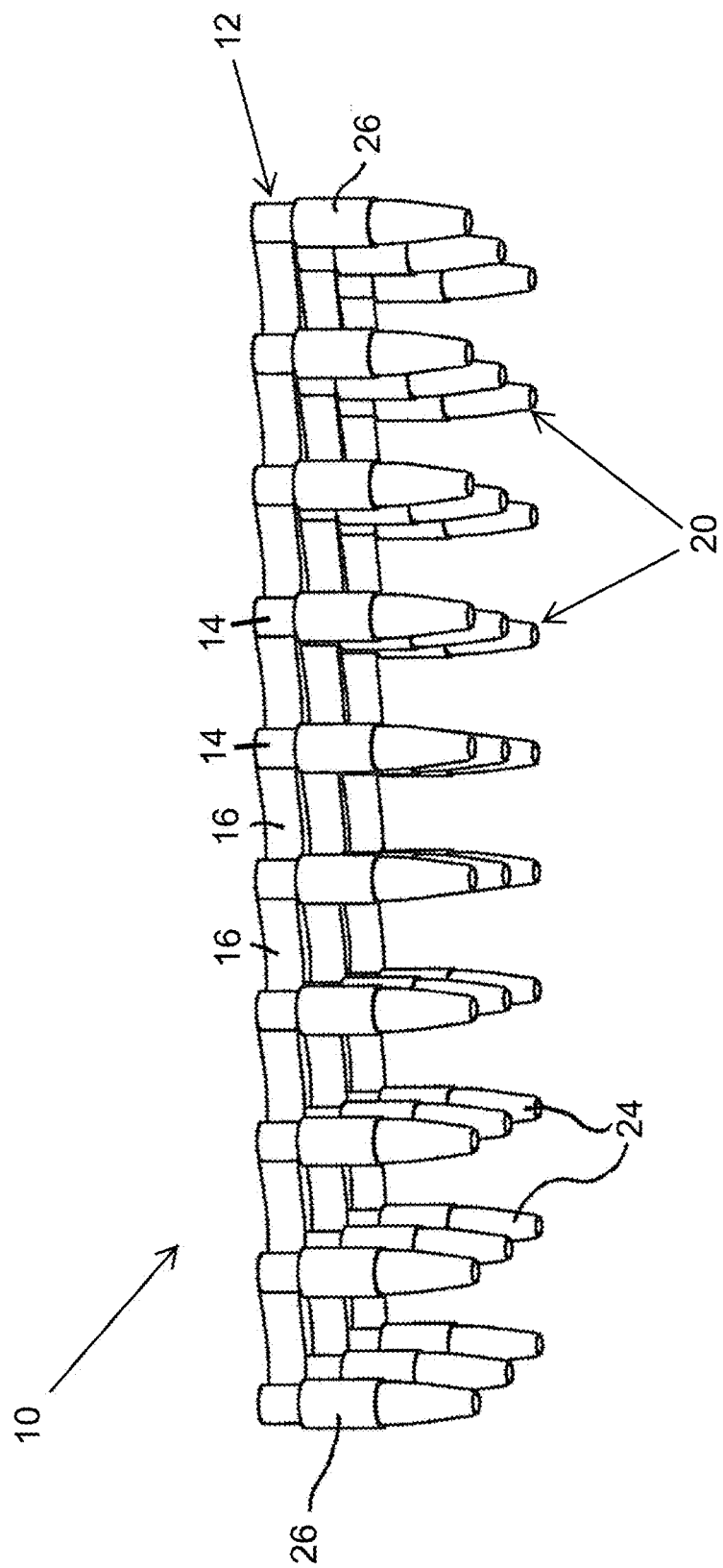
FIG. 3 schematically represents another nonlimiting embodiment of an expanded but collapsible cellular array structure and permeable inserts placed in each of a plurality of cells of the cellular array structure to form a collapsible basket array suitable for use with multi-well plates of types used for culture and histology analysis of spheroids and organoids.

FIG. 3 schematically represents another nonlimiting embodiment of a collapsible basket array 10. In view of similarities between the embodiments of FIGS. 1 and 3, aspects of the embodiment of FIG. 3 not discussed in any detail can be, in terms of structure, function, materials, etc., essentially as was described for the embodiment of FIG. 1. In contrast to the embodiment of FIG. 1, each of the cells 14 and connectors 16 of the cellular array structure 12 of FIG. 3 has a flat strip-like configuration with a rectangular cross-section. Similar to the embodiment of FIG. 1, the cells 14 of the cellular array structure 12 are generally circular-shaped, but in the form of a tube that defines and surrounds a central opening. Each insert 20 comprises a basket 24 and a heat shrink sleeve 26 that secures the basket 24 to a portion of the tubular form of its insert 20 that protrudes from the plane of its connectors 16. Each basket 24 is in the form of a conical-shaped permeable or semipermeable membrane, though other configurations are foreseeable.

As more apparent from FIGS. 4 through 6, the connectors 16 are generally S-shaped (approximating a sigmoid curve), with oppositely-disposed halves or ends 16A and 16B of each connector 16 being attached to a different cell 14. More particularly, the ends 16A and 16B of each connector 16 are attached to two adjacent cells 14, but on opposite sides of the cells 14. For example, the cell 14 in the upper righthand corner of the cellular array structure 12 in FIG. 4 and the immediately adjacent cell 14 below it are interconnected with a connector 16 whose ends 16A and 16B are attached at roughly the 3 o'clock and 9 o'clock positions, respectively, of the upper and lower cells 14. Each cell 14 is likewise interconnected with each of its immediately adjacent cell 14 with an individual connector 16. As a result, each cell 14 located in a corner of the cellular array structure 12 is interconnected with two adjacent cells 14 by two connectors 16, each cell 14 located along an interior side of the cellular array structure 12 is interconnected with three adjacent cells 14 by three connectors 16, and each cell 14 located within the interior of the cellular array structure 12 is interconnected with four adjacent cells 14 by four connectors 16, as evident from FIGS. 4 through 6.

The cellular array structure 12 is represented in an expanded configuration in FIG. 5, which enables the cells 14 of the array structure 12 to be individually aligned with a well 32 of a well plate 30, as schematically represented in FIG. 6. The shapes of the connectors 16 are intended to elastically pull the cells 14 toward each other to acquire the collapsed configuration shown in FIG. 4. By comparing FIGS. 4 and 5, it can be seen that the cells 14 have been collapsed toward each other with minimal or no rotation of the cells 14, e.g., the ends 16A and 16B of the connector 16 interconnecting the two aforementioned cells 14 discussed above in reference to FIG. 4 remain positioned at roughly the 3 o'clock and 9 o'clock positions, respectively, of the upper and lower cells 14. Notably, the connectors 16 are preferably adapted to bias the cellular array structure 12 to the collapsed configuration, so that an external force is required to expand the cellular array structure 12 seen in FIG. 4 to acquire the expanded configuration seen in FIGS. 5 and 6. The collapsed configuration of the cellular array structure 12 seen in FIG. 4 is preferably capable of reducing the size of the array structure 12 for storage, transport, etc., for example, to the size of a histology cassette.

The cellular array structure 12 may be fabricated in an expanded state, followed by plastically deforming the connectors 16 so that thereafter the cellular array structure 12 is elastically biased toward the collapsed configuration (e.g., FIG. 4) and external forces are required to elastically expand the array structure 12 toward its expanded configuration (e.g., FIGS. 5 and 6). Alternatively, the cellular array structure 12 may be fabricated in a collapsed state, so that the cellular array structure 12 is elastically biased toward the collapsed configuration (e.g., FIG. 4) in its original state and only elastic deformation of the connectors 16 occurs as the cellular array structure 12 is forcibly expanded toward its expanded configuration (e.g., FIGS. 5 and 6). In either case, the cells 14 and connectors 16 can be fabricated from various different materials and using various fabrication processes, including but not limited to 3D printing using a print system suitable for manufacturing the cells 14 and the more pliable connectors 16. Fabrication and mechanical testing of certain prototypes of the cellular array structure 12 were successfully completed using polymer resins commercially available under the names OBJET Verowhiteplus RGD835 or POLYJET TangoBlack FLX973, from Stratasys Direct, Inc.

The conceptual design of a cellular array structure 12 and inserts 20 were fulfilled through a process of design, mechanical analysis, and fabrication of the cellular array structures 12, which as used herein are defined as a structure in which thin-walled material elements are connected to each other such that there are empty spaces between them. On application of an external force, such a cellular structure undergoes a shape transformation associated with a significant volume change, as evident from comparing FIG. 4 with FIG. 5. The cellular array structure 12 was designed as shown to comprise individual cells 14 that are connected to each other by the connectors 16, whose arrangement and arcuate shapes enable the cellular array structure 12 to deform in a specific desired manner to accomplish a large geometry change (as a nonlimiting example, approximately 400% strain). Again, by comparing FIGS. 4 and 5, it can be seen that, by removing an external biaxial tensile force on the cellular array structure 12 that causes the array structure 12 to acquire its expanded configuration (FIG. 5), the opposite ends 16A and 16B of each connector 16 partially wrap along a portion of the cell 14 to which the end 16A or 16B is connected as the array structure 12 collapses to its collapsed configuration (FIG. 4). In the nonlimiting embodiment of FIGS. 4 and 5, approximately one-half (each end 16A and 16B) of each connector 16 is wrapped along approximately one-fourth of the perimeter or circumference of the cell 14 to which it is connected as the array structure 12 collapses to its collapsed configuration.

Figure 12:
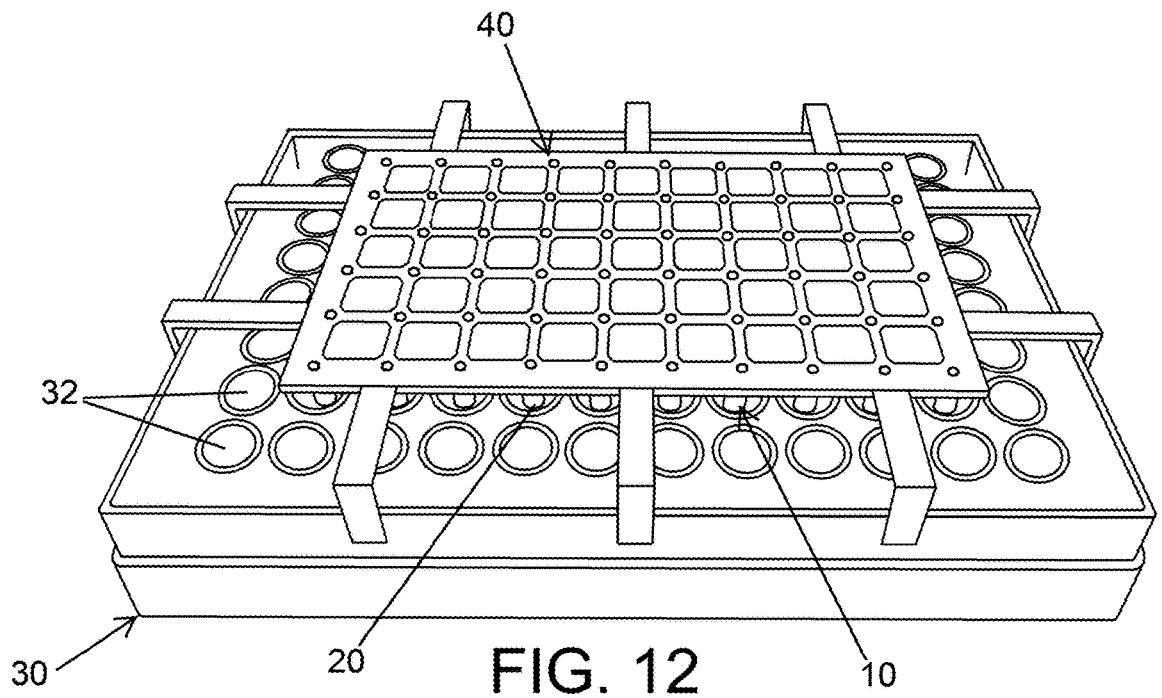
FIG. 12 depicts the collapsible basket array of FIG. 11 assembled with the spacer grid of FIGS. 7 and 8, and the resulting assembly positioned over a multi-well plate.
Figure 13:
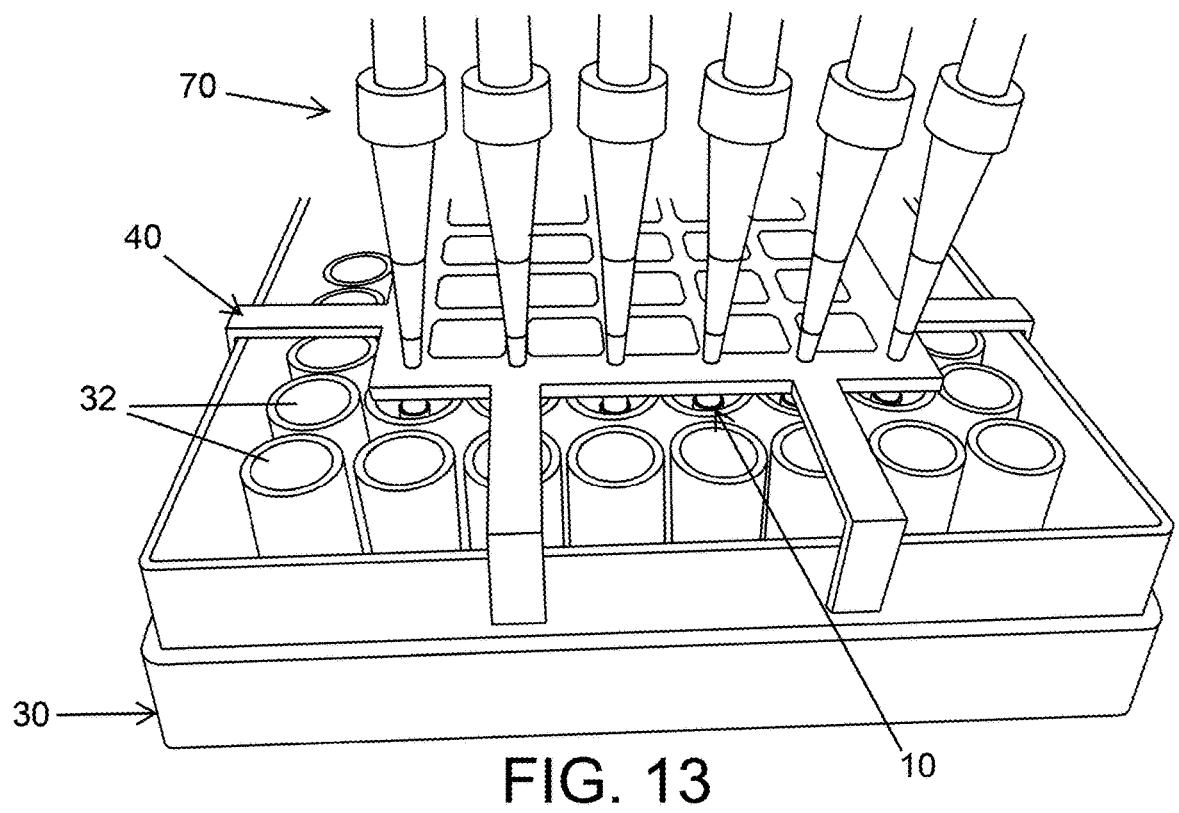
FIG. 13 demonstrates compatibility of the collapsible basket array and spacer grid with the use of a multi-channel pipette.

Designs of suitable inserts 20 were also fulfilled through a process of design, mechanical analysis, and fabrication. Inserts 20 having baskets 24 of various types and construction (e.g., the cups and membranes of FIGS. 2 and 3) are foreseeable, as are means (e.g., the arms 22 or sleeves 26 of FIGS. 2 and 3) that secure the baskets 24 to the array structure 22. In each case, the baskets 24 are capable of retaining spheroids or organoids during culturing while preferably enabling culture media and any solutes to freely diffuse therethrough. Various diameters for the basket 24 are foreseeable, as are pore sizes for the basket 24. The arms 22 and sleeves 26 preferably attach their respective baskets 24 to a cell 14 so that the position of the insert 20 and its basket 24 will be maintained after the insert 20 is attached to the cell 14, and no deformation will occur adjacent to spheroids and organoids within in the basket 24. Thus, the morphology of spheroids and organoids are can be protected throughout the process. In addition, the baskets 24 are preferably designed so that the bottom of each basket 24 will be suspended above the bottom interior surface of a well 32 in which it is placed (FIGS. 12 and 13). Additionally, the bottom of each basket 24 is preferably U-shaped to facilitate spheroid/organoid formation. Nylon is believed to be suitable as the material for the basket 24 due to being commercially available in a wide range of pore sizes (e.g., about 5 to about 100 μm), its ease of sterilization and fabrication, and its biocompatibility with culturing mammalian cells. Furthermore, surfaces of a nylon basket 24 can be coated with, as nonlimiting examples, agarose, poly-2-hydroxyethyl methacrylate (poly-HEMA), or Matrigel to induce cellular aggregations. [2-4]. As an alternative to nylon, other materials could foreseeably be used, as a nonlimiting example, polycarbonate.

Figure 8:
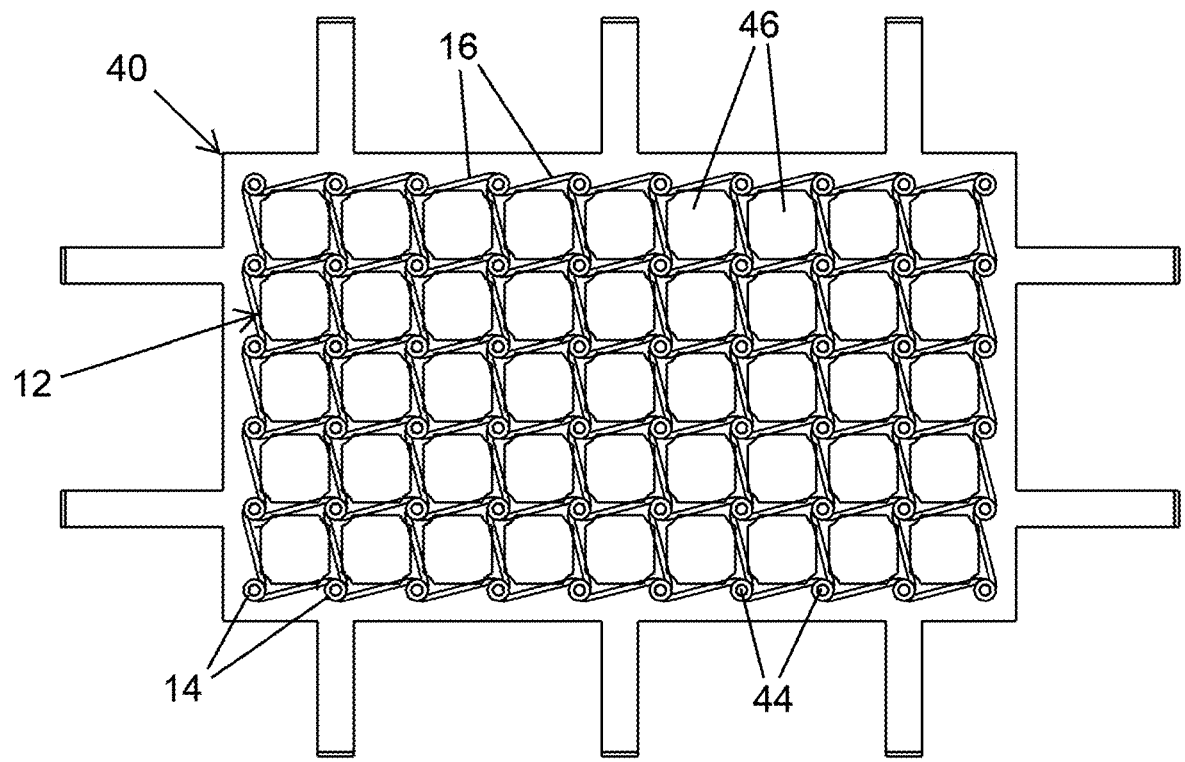
FIG. 8. schematically represents a collapsible cellular array structure installed on the spacer grid of FIG. 7, whereby the spacer grid applies biaxial forces that expand and maintain the collapsible cellular array structure in its expanded configuration.

FIGS. 7 through 11 depict various fixtures and tools adapted for use with collapsible cellular array structures of types represented in FIGS. 1 through 6, and FIGS. 12 and 13 depict nonlimiting examples of uses of collapsible basket arrays of types represented in FIGS. 1 through 6. FIGS. 7 and 8 schematically represent a spacer grid 40, and FIG. 8 represents a collapsible cellular array structure 12 mounted to the spacer grid 40 of FIG. 7. The grid 40 comprises a rectangular-shaped frame 42 with arrays of two apertures 44 and 46 and legs 48 extended outward from the frame 42. As seen in FIG. 8, the cellular array structure 12 has been expanded so that its cells 14 are individually aligned with the smaller apertures 44 of the grid 40 and its central openings are individually aligned with the larger apertures 46 of the grid 40.

Figure 9:
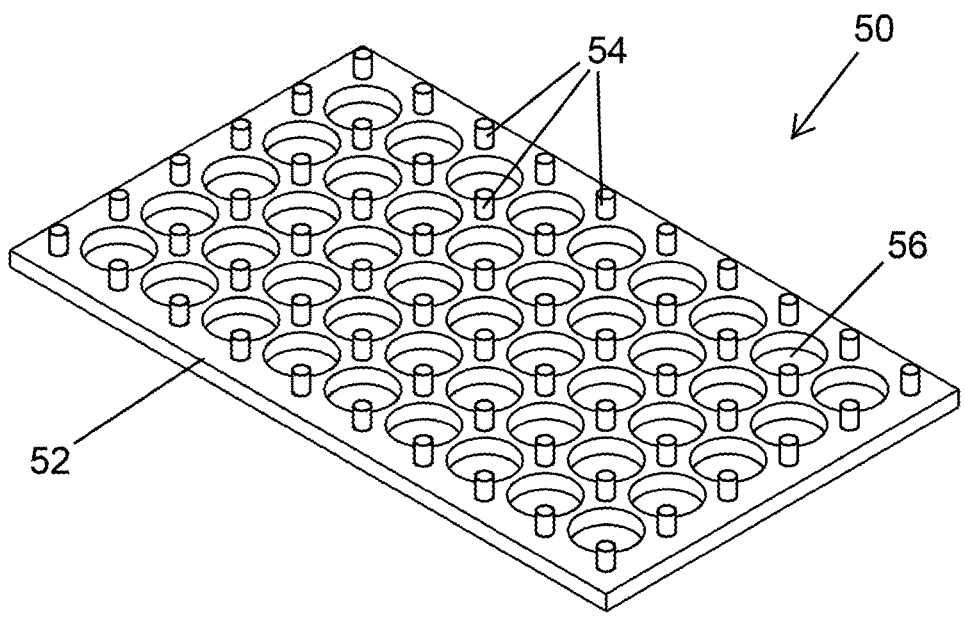
FIG. 9 schematically represents a separator plate configured and adapted to remove and release the cellular array structure from the spacer grid of FIGS. 7 and 8.

FIG. 9 schematically represents a separator plate 50 having pins 54 that are located between apertures 56 in the separator plate 50. The pins 54 are located and sized to individually align with the apertures 44 of the spacer grid 40. The cellular array structure 12 mounted to the spacer grid 40 as shown in FIG. 8 can be released from the spacer grid 40 by pressing the pins 54 of the separator plate 50 into the apertures 44 of the spacer grid 40. The array structure 12 is in the expanded configuration when installed on the spacer grid 40 (FIG. 8) and secured to the spacer grid 40 as a result of tension in the elastically deformed connectors 16. As a result, the separator plate 50 can be used to release the constraint provided by spacer grid 40, allowing the elastic energy (deformation) stored in the connectors 16 to be released so that the array structure 12 spontaneously returns (collapses) to the collapsed configuration.

Figure 10:
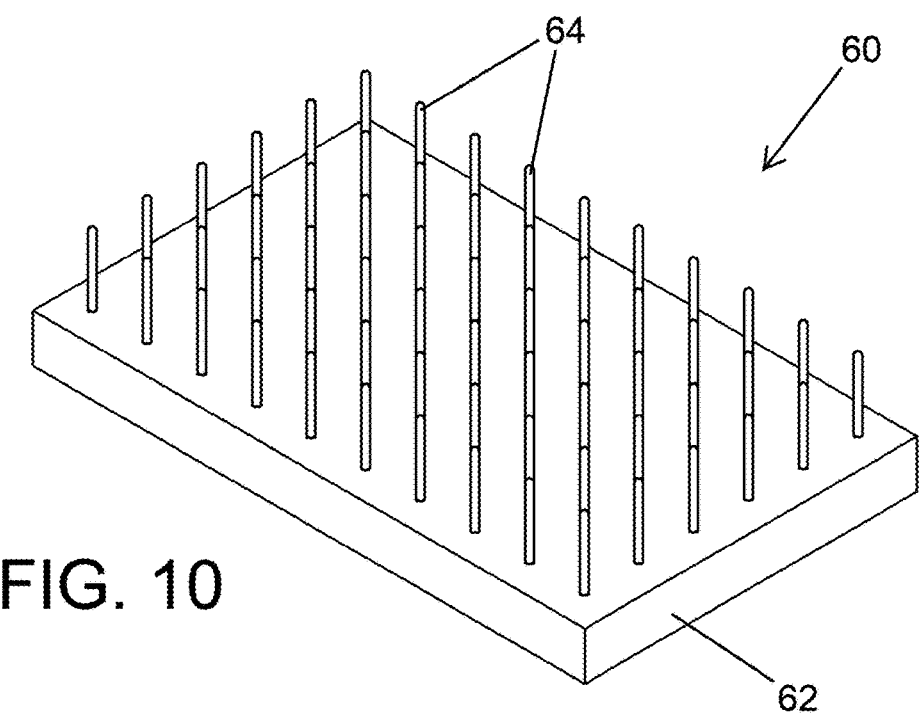
FIG. 10 schematically represents an array mold adapted to enable inserts to be assembled to a collapsible cellular array structure while the cellular array structure is maintained in its expanded configuration by pins of the array mold.
Figure 11:
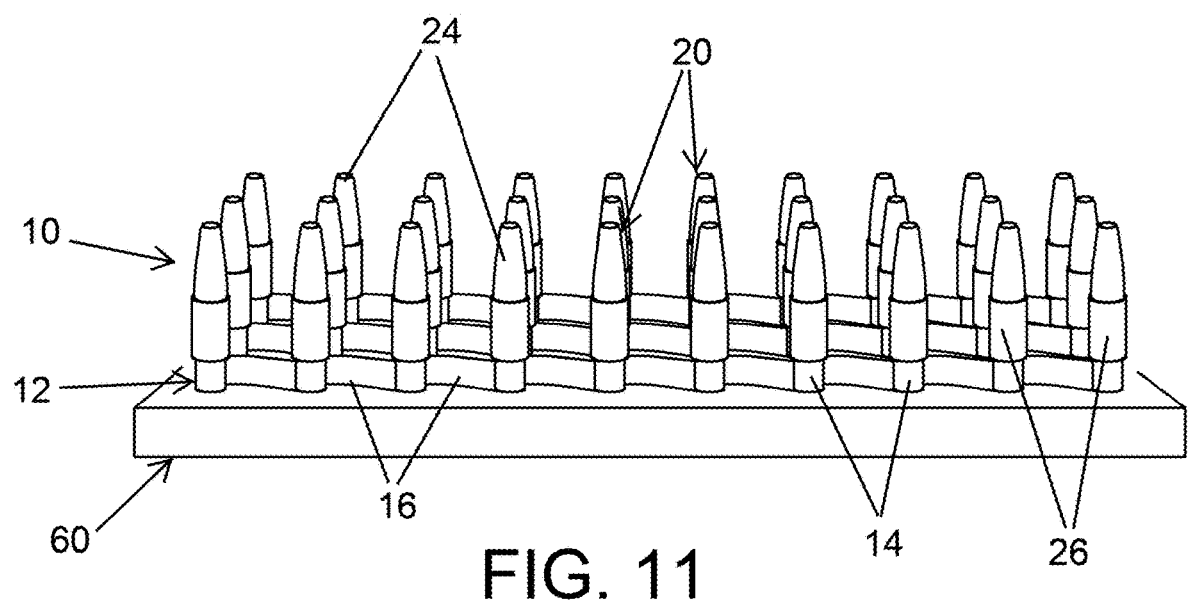
FIG. 11 schematically represents a collapsible basket array installed on the array mold of FIG. 10, the cellular array structure of the collapsible basket array maintained in its expanded configuration by pins of the array mold, and inserts of the collapsible basket array individually attached to cells of the cellular array structure with heat shrink tubes.

For assembly of the inserts 20 to the cellular array structure 12, the cellular array structure 12 is expanded by being fixtured on an array mold 60, schematically represented in FIGS. 10 and 11. FIG. 10 represents the mold 60 as comprising a base 62 with an array of pins 64 that extend upward from the base 62. As seen in FIG. 11, the cellular array structure 12 of FIG. 3 has been expanded so that the central openings of its cells 14 are individually aligned with and receive the pins 64 of the mold 60. FIG. 11 further represents the inserts 20 secured to their respective cells 14 with the heat shrink tubes 26.

FIG. 12 schematically represents the fully assembled and expanded basket array 10 of FIG. 11 mounted to and beneath the spacer grid 40, which positions the basket array 10 over a multi-well plate 30 so that the inserts 20 of the basket array 10 are individually received in the wells 32 of the plate 30. Finally, FIG. 13 illustrates the compatibility of the assembled collapsible basket array 10 and spacer grid 40 with the use of a multi-channel pipette 70.

As previously noted, the basket array 10 is secured to the spacer grid 40 as a result of tension in the elastically deformed connectors 16. This tension allows the spacer grid 40 to lift the basket array 10 from the well plate 30 of FIGS. 12 and 13 to replace media or add testing reagents for drug screening in cultured spheroids or organoids within the baskets 24 of the inserts 20, or to transfer spheroids or organoids cultured with the well plate 30 to another well plate. Following the processes depicted in FIGS. 12 and/or 13, the basket array 10 can be collapsed for placement in a cassette by using the pins 54 of the separator plate 50 to push the array structure 12 from the spacer grid 40, thereby removing and releasing the cellular array structure 12 from the spacer grid 40 and allowing the biasing effect of the connectors 16 of the cellular array structure 12 to biaxially and uniformly collapse the entire cellular array structure 12 while the inserts 20 assembled thereto remain attached to and suspended from the cells 14.

Figure 16:
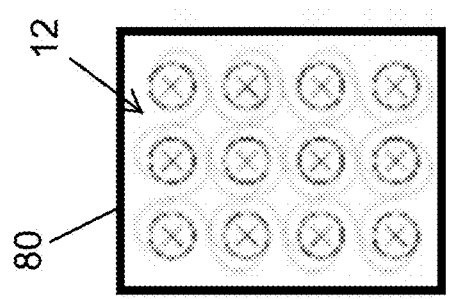
FIGS. 14, 15, and 16 schematically represent, respectively, a collapsible basket array in its collapsed configuration, the collapsible basket array of FIG. 14 after it has been expanded to its expanded configuration and after inserts thereof have been individually registered with wells of a multi-well plate, and the collapsible basket array of FIG. 15 placed in a cassette after the collapsible basket array has been collapsed to reacquire its collapsed configuration.
Figure 15:
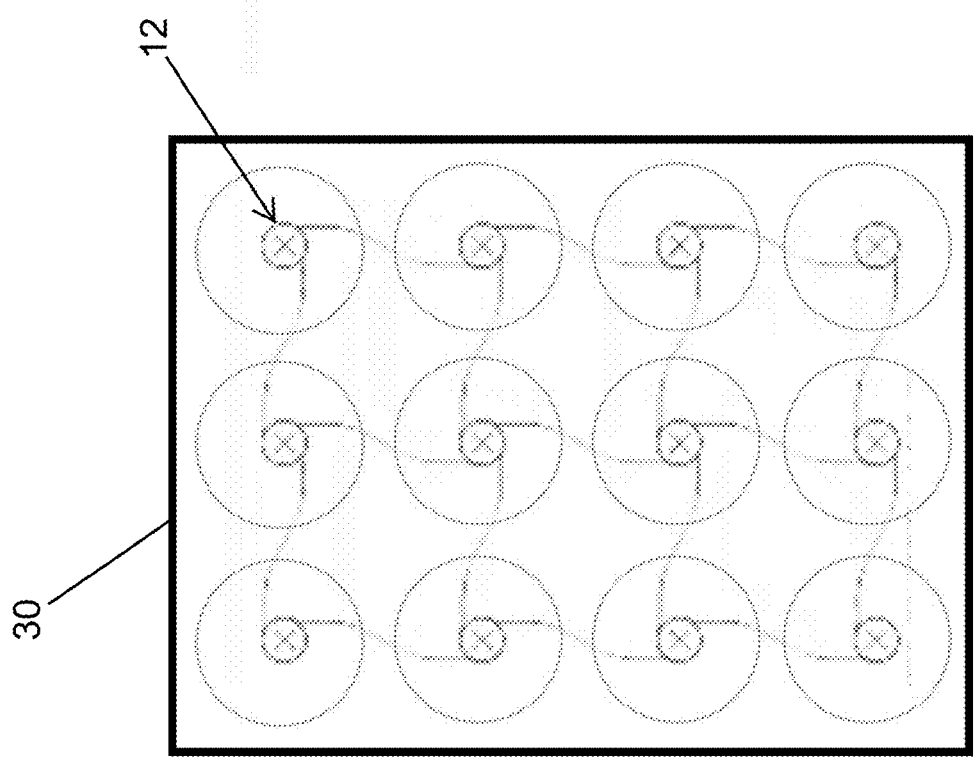
Figure 14:
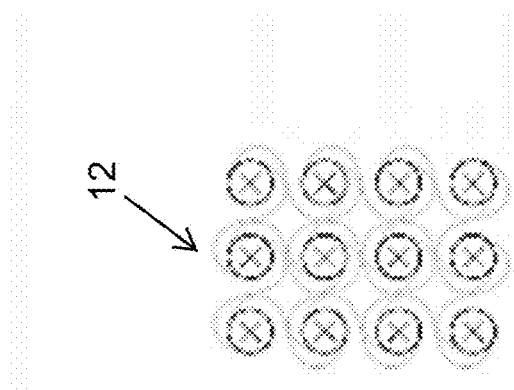

In view of the above, cultured spheroid or organoid contained in the baskets 24 of the inserts 20 can be directly transferred from the well plate 30 of FIGS. 12 and 13 to a cassette or another component that may be utilized for high throughput analysis. To illustrate, FIGS. 14, 15, and 16 schematically represent, respectively, a collapsible basket array 10 in its collapsed configuration, the collapsible basket array 10 of FIG. 14 after it has been expanded to its expanded configuration and its inserts 20 individually registered with wells 32 of a multi-well plate 30, and the collapsible basket array of FIG. 15 placed in a cassette 80 after the collapsible basket array 10 has been collapsed to reacquire its collapsed configuration While the invention has been described in terms of specific or particular embodiments and investigations, it should be apparent that alternatives could be adopted by one skilled in the art. For example, the collapsible basket arrays and their collapsible cellular array structures and inserts could differ in appearance and construction from the embodiments described herein, and various materials and processes could be used for their fabrication. Accordingly, it should be understood that the invention is not necessarily limited to any embodiment described herein. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A collapsible basket array for culture and histology analysis of spheroids or organoids, the collapsible basket array comprising:
a collapsible cellular array structure comprising multiple cells and connectors that interconnect adjacent pairs of the cells to cause the collapsible cellular array structure to spontaneously and biaxially collapse from an expanded configuration to a collapsed configuration in which the connectors are partially wrapped around perimeters of the cells, the connectors being elastically deformable and connected to the cells to enable the cells to rotate when the collapsible cellular array structure is expanded to the expanded configuration and spontaneously and biaxially collapses to the collapsed configuration, the collapsible cellular array structure being expandable to acquire the expanded configuration capable of individually aligning the cells thereof with wells of a well plate; and
a plurality of inserts individually mountable to the cells of the collapsible cellular array structure, the inserts each comprising a permeable or semipermeable basket having pores sized to retain spheroids or organoids within the baskets.

2. The collapsible basket array according to claim 1, wherein the cells are circular in shape and in the collapsed configuration the connectors are partially wrapped around circumferences of the cells.

3. The collapsible basket array according to claim 1, wherein each of the connectors has opposite ends and each of the ends partially wraps along a portion of the perimeter of the cell to which the end is connected as the collapsible cellular array structure spontaneously and biaxially collapses to the collapsed configuration.

4. The collapsible basket array according to claim 3, wherein about one-half of each of the connectors is wrapped along about one-fourth of the perimeter of the cell to which the connector is connected as the collapsible cellular array structure spontaneously and biaxially collapses to the collapsed configuration.

5. The collapsible basket array according to claim 1, wherein the connectors are S-shaped and each of the connectors is attached to opposite sides of the adjacent pairs of the cells that the connector interconnects.

6. The collapsible basket array according to claim 1, wherein each of the cells has a central opening.

7. The collapsible basket array according to claim 1, wherein each of the inserts further comprises arms that couple the basket thereof to one of the cells of the collapsible cellular array structure.

8. The collapsible basket array according to claim 1, wherein the cells each comprise a tubular portion and each of the inserts further comprises a heat shrink tube that couples the basket thereof to the tubular portion of one of the cells.

9. The collapsible basket array according to claim 1, wherein the collapsed configuration of the collapsible cellular array structure enables the collapsible basket array to be sufficiently collapsed for placement in a histology cassette.

10. The collapsible basket array according to claim 1, wherein the connectors are elastically deformable and elastically bias the collapsible cellular array structure to spontaneously and biaxially collapse from the expanded configuration to the collapsed configuration.

11. A system for directly transferring cultured spheroid or organoid into a histology cassette or other high throughput analysis configuration, the system comprising:
the collapsible basket array of claim 1;
a spacer grid configured to maintain the collapsible cellular array structure in the expanded configuration thereof; and
a separator plate configured to release the collapsible cellular array structure from the spacer grid to enable the collapsible basket array to spontaneously and biaxially collapse to the collapsed configuration.

12. A method of performing culture and histology analysis of spheroids or organoids using the collapsible basket array of claim 1, the method comprising:
expanding the collapsible cellular array structure to acquire the expanded configuration capable thereof;
individually aligning the inserts of the collapsible basket array with wells of a well plate and inserting the inserts individually into the wells of the well plate;
culturing spheroids or organoids in the baskets of the inserts;
displacing the collapsible basket array from the well plate to remove the inserts from the wells of the well plate;
spontaneously and biaxially collapsing the collapsible basket array to the collapsed configuration thereof; and
placing the collapsible basket array in a cassette.

13. The method according to claim 12, wherein the cells are circular in shape and in the collapsed configuration the connectors are partially wrapped around circumferences of the cells.

14. The method according to claim 12, wherein each of the connectors has opposite ends and each of the ends partially wraps along a portion of the perimeter of the cell to which the end is connected as the collapsible cellular array structure spontaneously and biaxially collapses to the collapsed configuration.

15. The method according to claim 14, wherein one-half of each of the connectors wraps along one-fourth of the perimeter of the cell to which the connector is connected as the collapsible cellular array structure spontaneously and biaxially collapses to the collapsed configuration.

16. The method according to claim 12, wherein the connectors are S-shaped and each of the connectors is attached to opposite sides of the adjacent pairs of the cells that the connector interconnects.

17. The method according to claim 12, wherein each of the cells has a central opening.

18. The method according to claim 12, further comprising coupling the inserts to the cells of the collapsible cellular array structure with arms of the inserts.

19. The method according to claim 12, wherein each of the cells comprises a tubular portion and the method further comprises coupling the inserts to the tubular portions of the cells with heat shrink tubes.

20. The method according to claim 12, wherein the connectors are elastically deformable and elastically bias the collapsible cellular array structure to spontaneously and biaxially collapse from the expanded configuration to the collapsed configuration.

* * * * *